(12) United States Patent
Sage et al.

(10) Patent No.: US 7,110,827 B2
(45) Date of Patent: Sep. 19, 2006

(54) ELECTRICAL CONNECTORS FOR MEDICAL LEAD HAVING WELD-LESS WIRING CONNECTION

(75) Inventors: Shahn S. Sage, Andover, MN (US); Jeffrey S. Gagnon, Champlin, MN (US); Jane L. Kohnen, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 508 days.

(21) Appl. No.: 10/423,107

(22) Filed: Apr. 25, 2003

(65) Prior Publication Data

US 2004/0215302 A1 Oct. 28, 2004

(51) Int. Cl.
*A61N 1/00* (2006.01)

(52) U.S. Cl. .................. 607/116; 439/909; 607/115

(58) Field of Classification Search ............ 607/115, 607/36–38, 119, 116–122, 1; 439/909, 881, 439/668, 669, 841, 877
See application file for complete search history.

(56) References Cited

U.S. PATENT DOCUMENTS

| | | | | |
|---|---|---|---|---|
| 4,355,646 A * | 10/1982 | Kallok et al. | ............... | 607/122 |
| 4,381,014 A * | 4/1983 | Sandstrom et al. | ......... | 607/119 |
| 4,707,566 A * | 11/1987 | Titcombe et al. | ............. | 174/78 |
| 4,934,366 A * | 6/1990 | Truex et al. | ................... | 607/37 |
| 5,411,348 A | 5/1995 | Balsells | ...................... | 403/326 |
| 5,474,309 A | 12/1995 | Balsells | ...................... | 277/163 |
| 5,503,375 A | 4/1996 | Balsells | ...................... | 267/167 |
| 5,532,436 A * | 7/1996 | Moyers et al. | ............... | 174/151 |
| 5,545,842 A | 8/1996 | Balsells et al. | ............... | 174/35 |
| 5,575,487 A | 11/1996 | Balsells | ...................... | 277/169 |
| 5,584,873 A * | 12/1996 | Shoberg et al. | ............. | 607/122 |
| 5,599,027 A | 2/1997 | Balsells | ...................... | 277/163 |
| 5,615,870 A | 4/1997 | Balsells | ...................... | 267/167 |
| 5,709,371 A | 1/1998 | Balsells | ...................... | 267/167 |
| 5,791,638 A | 8/1998 | Balsells | ...................... | 267/167 |
| 5,979,904 A | 11/1999 | Balsells | ...................... | 277/554 |
| 5,984,316 A | 11/1999 | Balsells | ...................... | 277/553 |
| 5,992,856 A | 11/1999 | Balsells et al. | ............. | 277/553 |
| 6,050,572 A | 4/2000 | Balsells et al. | ............. | 277/551 |
| 6,161,838 A | 12/2000 | Balsells | ...................... | 277/511 |
| 6,264,205 B1 | 7/2001 | Balsells | ...................... | 277/551 |
| 2002/0099430 A1* | 7/2002 | Verness | ...................... | 607/122 |
| 2002/0115343 A1* | 8/2002 | Sommer et al. | ............ | 439/578 |
| 2002/0193859 A1* | 12/2002 | Schulman et al. | .......... | 607/116 |
| 2004/0093038 A1* | 5/2004 | Biggs et al. | .................. | 607/37 |
| 2004/0215303 A1* | 10/2004 | Sage | .......................... | 607/116 |

OTHER PUBLICATIONS

Bal Seal Engineering, "Bal Contact Advantage," Foothill Ranch, CA 2002, pp. 1-19.

* cited by examiner

*Primary Examiner*—George R. Evanisko
*Assistant Examiner*—Stephanie Smith
(74) *Attorney, Agent, or Firm*—Fredrikson & Byron, PA

(57) ABSTRACT

Low resistivity, implantable electrical connectors and biomedical leads having the connectors mechanically coupled in a non-welded attachment to low resistivity wires to extend implanted device battery life. One electrical connector includes an electrically conductive housing having a longitudinal aperture and an inner facing circumferential channel. A spring disposed within the channel can contact an inserted electrode. The housing can include at least one hole adjacent a mechanically deformable side wall for mechanically securing an electrical conductor inserted within the hole. The low resistivity, implantable, biocompatible electrical connectors and leads can be used in neurological and cardiac applications.

14 Claims, 2 Drawing Sheets

ELECTRICAL CONNECTORS FOR MEDICAL LEAD HAVING WELD-LESS WIRING CONNECTION

BACKGROUND OF THE INVENTION

1. Field of the Invention

The present invention is related generally to medical devices. More specifically, the present invention is related to implantable electrical connectors that find one use in neurological stimulation leads.

2. Description of Related Art

Neurological stimulation leads are increasingly used in a variety of applications. One common use for neurological stimulation leads is paresthesia, the stimulation of the spinal cord from within the spine through the application of artificially generated electrical signals. This artificial stimulation can be used to control pain in chronic pain patients by effectively masking pain signals at the spine.

A neurological stimulation lead is commonly used to deliver electrical signals. One such lead is formed of polymeric material, for example, polyurethane or silicone. The lead can be nominally 1 mm in outer diameter and about 20 cm in length. A typical lead may have a series of electrodes formed as bands or rings disposed in a spaced apart relationship in a lead distal region. The distal region of the lead can later be introduced into the spinal column. One exemplary lead may have eight electrodes in the distal region, with each electrode having its own conductor extending along the length of the lead to a lead proximal region. The lead proximal region of the lead can have a corresponding set of band or ring connectors, one for each corresponding electrode in the distal region. Each proximal region connector can thus be connected to one distal electrode in a typical configuration. The connectors can be used to couple the proximal end of the lead to a lead extension that can in turn be coupled to an implantable pulse generator (IPG).

A typical connector is an electrical connector serving as a male electrical connection, adapted to be received within a corresponding female electrical connector in a lead extension. One such female electrical connector includes a cylindrical outer housing having a transverse circumferential groove or channel within the interior face of the housing. A metallic coil spring can be disposed within the circumferential channel, providing electrical continuity between the spring and the outer metallic housing. Electrical connectors of this type are available from Bal Seal Engineering Company, Inc., Foothill, Calif., USA. The male connector bearing an electrically conducting outer surface can be suitably dimensioned to be insertable through the spring with minimum force. The spring can provide a radially inward directed force on the male connector outer surface to establish contact between the male connector and the spring. In one lead extension proximal region, a set of seven, spring loaded, tool-less connectors are aligned coaxially with each other, along with a single connector, which includes a set screw to mechanically fix the inserted lead within the lead extension. The seven tool-less lead extension connectors can be imbedded within the tube or be covered with an insulating sleeve or boot. The set screw lead extension connector is typically insulated to prevent unwanted electrical contact with the body.

The eight lead extension proximal connectors can thus be electrically coupled to eight corresponding connectors of an inserted lead. The lead extension can provide added length to extend the reach of the lead to a more distantly placed IPG. Some lead extensions are between about 20 and 50 cm in length.

Neurological leads are increasingly used, and implanted for long periods of time. The IPG is most typically powered by a battery that is implanted with the IPG. In some IPGs, the batteries or IPGs themselves can receive power input through the skin through radio frequency (RF) energy from a transmitter disposed outside of the patient. In the majority of cases however, the IPG has an implanted battery with a limited life.

The battery life of the IPG is dependent upon the current delivered to the electrode distal end and upon the electrical losses in the conductors between the IPG and the lead distal end. Current lead conductors utilize MP35N, a nickel alloy widely used because of its biocompatible characteristics. While nickel alloy is a good material in many respects, it has the less than optimal property of moderate electrical resistivity. This means that some of the battery power goes to resistive heating of the nickel alloy wires, rather than to pain relief.

The nickel alloy wires are typically each welded to a connector, a practice of long standing that has previously proved suitable, but uses wire having moderate resistivity. Silver or silver core wires having a lower resistivity than nickel alloy can be used. The silver wires can also be welded, but present a problem. The silver can oxidize and turn brittle, a less than optimal property. For this reason, among others, the wire typically has a silver core clad in a nickel alloy, for example, MP35N. The nickel alloy clad silver core wire can also be welded, but the welding itself can present difficulties. The silver has a lower melting point that the surrounding nickel alloy. When such nickel alloy clad silver core wire is welded, the silver core can melt prior to the nickel alloy, puddle, and contaminate the weld.

The current two piece connectors also add resistivity by nature of their two piece construction, as there is some resistance in the electrical path between the two pieces. Specifically, while the outer housing and inner spring may both be metallic, the electrical contact between the two is not perfect.

What would be most advantageous are implantable leads having very low resistance in an assembly having a conductor connected to the connector. What would be desirable are neurological lead extensions and connectors that allow for use of silver core wire in order to increase battery life of implanted IPGs.

SUMMARY OF THE INVENTION

The present invention provides an implantable electrical connector including an electrically conductive outer housing having a longitudinal aperture and a transverse inner facing circumferential channel disposed about the longitudinal aperture, and an electrically conductive resilient member disposed within the housing channel and in electrical communication with the housing. The housing can include at least one hole formed in the housing adjacent to at least one mechanically deformable side wall for mechanically securing an electrical conductor inserted within the hole. In some connectors the hole is a blind hole, and in others extends entirely through the housing and is substantially parallel to the longitudinal axis. The resilient member is a coiled metallic spring in some connectors. The connector housing preferably has no dimension larger than about one quarter inch and is formed of a bio-compatible, electrically conductive material.

The present invention also provides an implantable electrical connector assembly including an electrical conductor mechanically attached to the electrical connectors in a non-welded attachment. The electrical conductor can have a portion inserted within a connector hole and be mechanically secured to the housing by a non-welded, mechanical deformation of a side wall against the inserted conductor portion. The mechanical deformation can be a stake in some embodiments and a crimp in other embodiments. The conductor can be a silver core wire, a nickel alloy cladding over a silver core wire, a bundle of nickel alloy clad silver core wires, or another conductor material.

The present invention also provides an implantable electrical lead including an implantable electrical lead assembly as previously described and an implantable lead body. The implantable electrical lead can include an elongate lead body including a proximal region, a distal region, and having a lumen disposed through at least the lead body proximal region. The lead can also include at least one conductor disposed within the lead body and extending from the proximal region to the distal region. The lead can include at least one electrical connector disposed in the lead body proximal region, wherein the connector is electrically coupled to the conductor in a non-welded mechanical attachment. The lead preferably includes at least one distal contact disposed in the lead body distal region and an electrical contact but with the at least one conductor.

DETAILED DESCRIPTION

The following detailed description should be read with reference to the drawings, in which like elements in different drawings are numbered identically. The drawings, which are not necessarily to scale, depict selected embodiments and are not intended to limit the scope of the invention. Several forms of invention have been shown and described, and other forms will now be apparent to those skilled in art. It will be understood that embodiments shown in drawings and described below are merely for illustrative purposes, and are not intended to limit the scope of the invention as defined in the claims that follow.

Figure 1:
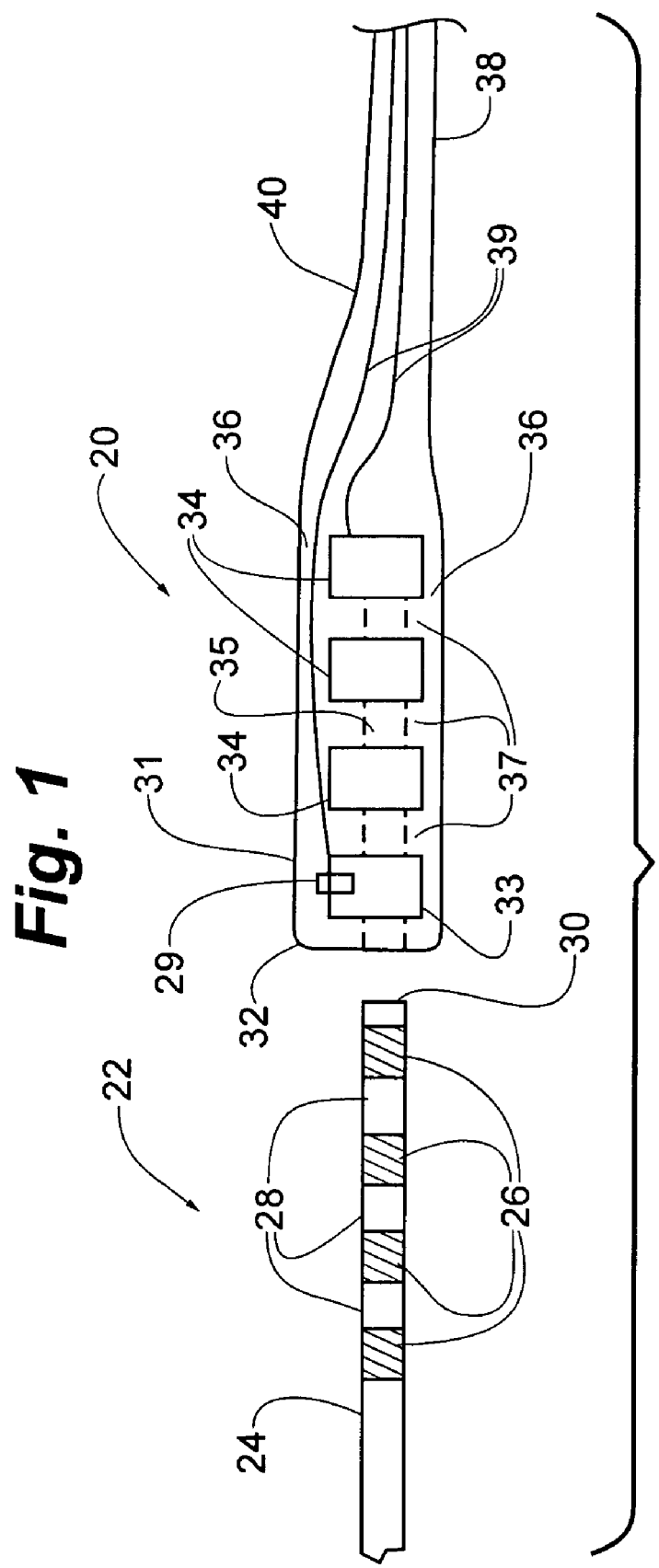
FIG. 1 is a fragmentary side view of an electrical lead oriented for insertion into an electrical lead extension, with the lead extension being cut away to reveal four electrical connectors according to the present invention.

FIG. 1 illustrates an electrical lead 22 positioned to be inserted within an electrical lead extension 20. Lead 22 represents any appropriate biomedical lead. Non-limiting examples include implanted or implantable neurological or cardiac leads. Lead 22 may be seen to have generally a body 24, a proximal end 30, and four external electrical connectors or bands 26, separated by non-conducting regions 28. The electrical connectors, bands, or electrodes 26 may be electrically coupled to four more distal portions of lead 22 through conductors (not visible in FIG. 1).

Lead extension 20 includes generally a body 40, extending from an intermediate region 38 through a proximal region 31 to a proximal end 32. Four electrical connectors, 33 and 34, may be seen within lead extension proximal region 31, separated therebetween by nonconductive regions 37. Nonconductive material 36, for example, polyurethane or silicone rubber, may also be seen disposed about electrical connectors 34. Material 36 may be formed as a sleeve or boot slid axially over the connectors and over part of the lead body in order to insulate the connector external faces from each other and from the external environment.

In some lead extensions, at least one of the electrical connectors is exposed through some the lead extension body material to allow tightening of the electrical connectors about an inserted lead. An example of such an electrical connector is connector 33 having a set screw 29 accessible from the exterior of the lead for mechanically securing an inserted lead. Material 36 can be slid over connectors 34, or 34 and 33, depending on the embodiment. A lumen 35 may be seen extending distally from proximal end 32 through the interiors of electrical connectors 33 and 34 for receiving electrical lead 22. Two electrical conductors 39 may be seen extending through lead body 40 and terminating at two electrical connectors. Other conductors (not visible in FIG. 1) can be secured to the other connectors. The lead extension illustrated in FIG. 1 can include any of the connectors later described in the present application.

Figure 2:
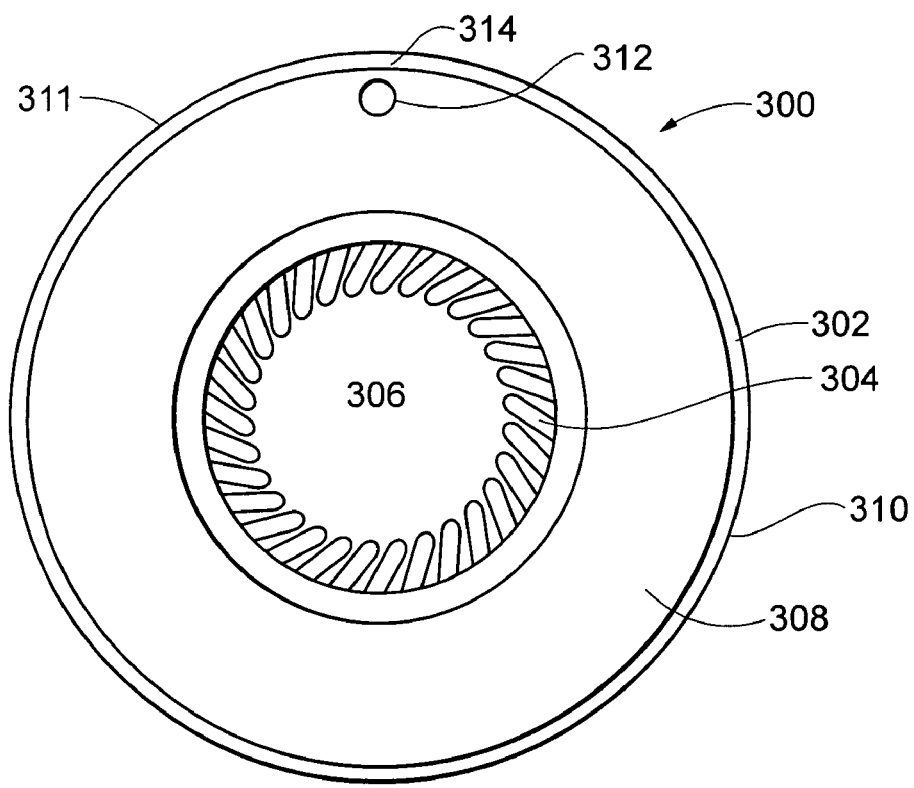
FIG. 2 is a side view of an electrical connector having an outer housing, an inner resilient spring, and a hole within a deformable side wall for mechanically attaching a conductor.

FIG. 2 illustrates one embodiment of the present invention in electrical connector 300. Electrical connector 300 includes an outer, cylindrical housing 302 having a central aperture 306 extending longitudinally therethrough. Connector 300 also includes a resilient spring member 304 disposed about central aperture 306 and within housing 302. Housing 302 and resilient spring member 304 are both preferably electrically conductive. Inspection of FIG. 2 illustrates how an inserted electrical connector would be put in electrical continuity with both the surrounding resilient spring 304 and, through the contact of spring 304 with housing 302, with housing 302. An end wall, lip, or flange 308 may be seen in FIG. 2 as may an outer, cylindrical, circumferential wall 310. A hole 312 may be seen formed into end wall 308. Hole 312 can be located a distance 314 from the outer wall surface 311. An electrical conductor, such as a wire, can be inserted into hole 312 and secured to connector 300.

A preferred method of securing a conductor inserted into hole 312 is the mechanical deformation of the side wall about hole 312 to mechanically fix the inserted conductor therein. The thin wall portion at 314 can be crimped in some embodiments and staked in other embodiments. When the inserted conductor is secured by staking, the wall can be mechanically deformed inward along primarily a single side of the conductor, or even about a single point against the wire. In some embodiments, hole 312 is a blind hole. In a preferred embodiment, hole 312 extends entirely, longitudinally through connector 300.

Figure 3:
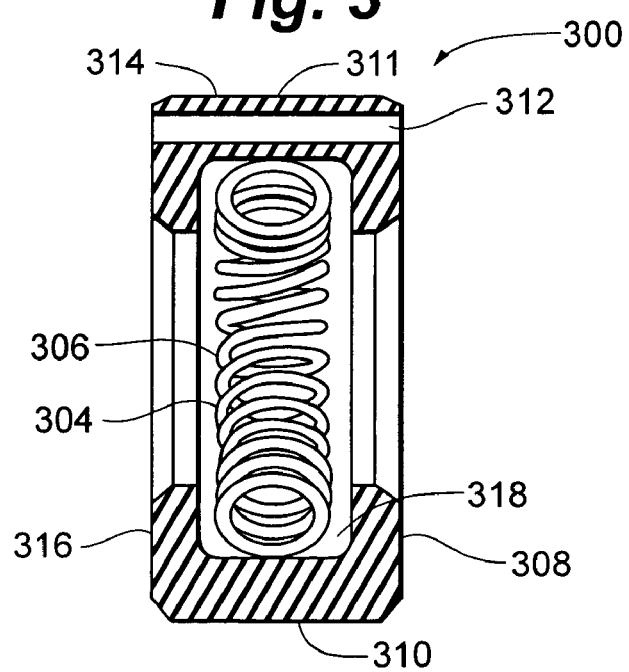
FIG. 3 is a longitudinal, cross sectional view of the electrical connector FIG. 2.

FIG. 3 illustrates connector 300 in a longitudinal, cross sectional view. A second end wall, flange or lip 316 may be seen opposed to first end wall 308. An annular, inner facing, circumferential channel 318 may be seen formed within circumferential outer wall 310. Spring 304 may be seen housed within annular groove or channel 318. Conductor insertion hole 312, when viewed from the side, illustrates the thinness of outer wall portion 314, forming the side wall of hole 312. Side wall portion 314, as previously described, can be deformed, for example, staked, against an inserted conductor wire. Connector body housing 302 can be formed of any suitable biocompatible material, for example, a nickel alloy such as MP35N. Spring 304 can also be formed of any suitable biocompatible material, for example, a nickel alloy such as MP35N. A preferred conductor is formed from a MP35N clad, silver core wire or a bundle of MP35N clad sliver core wires.

In one embodiment, housing 302 has an outer diameter of about 0.120 inch, an inner diameter of about 0.058 inch, and a transverse width of about 0.055 inch. Hole 312 can have a diameter of about 0.0065 inch, and a deformable wall thickness adjacent the hole of at least about 0.003 inch. In some embodiments, housing 302 has an outer diameter of less than about 0.25 inch, a transverse width of less than about 0.25 inch, and hole 312 can have a diameter of less than about 0.05 inch.

The invention claimed is:

1. An implantable electrical connector comprising:
   an electrically conductive housing having a longitudinal axis, a transverse dimension orthogonal to the longitudinal axis, a longitudinal aperture therethrough, and a transverse, inner facing circumferential channel therein disposed about the longitudinal aperture; and
   an electrically conductive resilient member disposed within the housing inner circumferential channel and in electrical communication with the housing,
   wherein the housing includes at least one hole formed therein adjacent at least one mechanically deformable sidewall for mechanically securing an electrical conductor inserted within the hole.

2. An electrical connector as in claim 1, wherein the hole is a blind hole.

3. An electrical connector as in claim 1, wherein the hole extends entirely through the housing.

4. An electrical connector as in claim 1, wherein the hole extends substantially parallel to the longitudinal axis.

5. An electrical connector as in claim 1, wherein the resilient member is a coiled metallic spring.

6. An electrical connector as in claim 1, wherein the housing has no dimension larger than about ¼ inch.

7. An implantable electrical connector assembly comprising:
   an electrically conductive housing having a longitudinal axis, a transverse dimension orthogonal to the longitudinal axis, a longitudinal aperture therethrough, and a transverse, inner facing circumferential channel therein disposed about the longitudinal aperture;
   an electrically conductive resilient member disposed within the housing inner circumferential channel and in electrical communication with the housing,
   wherein the housing includes at least one hole formed therein adjacent at least one mechanically deformable sidewall; and
   an electrical conductor having a portion inserted within the hole and mechanically secured to the housing by a non-welded, mechanical deformation of the sidewall against the inserted conductor portion.

8. An electrical connector assembly as in claim 7, wherein the mechanical deformation is a stake.

9. An electrical connector assembly as in claim 7, wherein the mechanical deformation is a crimp.

10. An electrical connector assembly as in claim 7, wherein the conductor is a silver core wire.

11. An electrical connector assembly as in claim 7, wherein the conductor includes a nickel alloy cladding over a silver core wire.

12. An electrical connector assembly as in claim 7, wherein the housing is substantially cylindrical and wherein the resilient member is a coiled metallic spring.

13. An implantable electrical lead comprising:
    an elongate lead body comprising a proximal region, a distal region, and having a lumen disposed through at least the lead body proximal region;
    at least one conductor disposed within the lead body and extending from the proximal region to the distal region;
    at least one electrical connector disposed in the lead body proximal region, wherein the connector comprises an electrically conductive body having a longitudinal aperture therethrough and an inner circumferential channel in the body about the longitudinal aperture to form a end lip on either side of the channel, and a conductive spring disposed at least partially within the channel and in communication with the longitudinal channel and lumen, wherein the outer and inner circumferential portions are in electrical communication with each other, wherein the connector is electrically coupled to the conductor in a non-welded mechanical attachment; and
    at least one distal contact disposed in the lead body distal region and in electrical contact with the at least one conductor.

14. An implantable lead as in claim 13, wherein the connector body includes at least one hole therein adjacent a mechanically deformable sidewall, and wherein the non-welded mechanical attachment includes the conductor being disposed within the hole and having the deformable sidewall mechanically deformed to close the hole about the inserted conductor.

\* \* \* \* \*